(12) United States Patent
Biedermann et al.

(10) Patent No.: US 8,696,712 B2
(45) Date of Patent: Apr. 15, 2014

(54) BONE ANCHORING DEVICE

(75) Inventors: Lutz Biedermann, VS-Villingen (DE); Wilfried Matthis, Weisweil (DE)

(73) Assignee: Biedermann Technologies GmbH & Co. KG, Donaueschingen (DE)

( * ) Notice: Subject to any disclaimer, the term of this patent is extended or adjusted under 35 U.S.C. 154(b) by 830 days.

(21) Appl. No.: 11/498,931

(22) Filed: Aug. 3, 2006

(65) Prior Publication Data

US 2007/0093818 A1   Apr. 26, 2007

Related U.S. Application Data

(60) Provisional application No. 60/704,992, filed on Aug. 3, 2005.

(30) Foreign Application Priority Data

Aug. 3, 2005   (EP) ..................................... 05016901

(51) Int. Cl.
*A61B 17/70* (2006.01)

(52) U.S. Cl.
USPC ........................................ 606/267; 606/270

(58) Field of Classification Search
USPC ........... 606/60, 246, 257, 264, 265, 267, 270, 606/274, 279, 305, 306, 308, 250–256, 606/258–263, 266, 268, 269, 271–273, 606/275–278, 300–304, 307, 309–321
See application file for complete search history.

(56) References Cited

U.S. PATENT DOCUMENTS

| | | | |
|---|---|---|---|
| 5,005,562 A | | 4/1991 | Cotrel |
| 5,443,467 A | * | 8/1995 | Biedermann et al. ........... 606/65 |
| 5,647,873 A | * | 7/1997 | Errico et al. ................... 606/264 |
| 5,899,904 A | * | 5/1999 | Errico et al. ................... 606/256 |

(Continued)

FOREIGN PATENT DOCUMENTS

| | | |
|---|---|---|
| CN | 1239414 A | 12/1999 |
| CN | 1241127 A | 1/2000 |

(Continued)

OTHER PUBLICATIONS

European Search Report for European Application No. 05016901.0-2318 dated Nov. 9, 2005, 7 pp.

(Continued)

*Primary Examiner* — Jerry Cumberledge
(74) *Attorney, Agent, or Firm* — Christie, Parker & Hale, LLP (57) ABSTRACT

A bone anchoring device includes an anchoring element with a shank to be anchored in a bone or a vertebra and a head. The anchoring device also includes a receiving portion with a first end and a second end opposite to the first end, a longitudinal axis passing through the two ends, a bore coaxial with the longitudinal axis, and a first region adjacent to the second end for receiving a section of said head. The anchoring device further includes an element which exerts pressure on said head to lock said head in the receiving portion. The receiving portion and the anchoring element are connected such that the longitudinal axis of the receiving portion and the shank axis have a fixed angle relative to each other. Additionally, the receiving portion and the shank are rotatable with respect to each other around the longitudinal axis and are locked in the rotational position when pressure is exerted on the head.

26 Claims, 4 Drawing Sheets

(56) References Cited

U.S. PATENT DOCUMENTS

| | | | |
|---|---|---|---|
| 5,938,663 A * | 8/1999 | Petreto | 606/278 |
| 6,010,503 A * | 1/2000 | Richelsoph et al. | 606/278 |
| 6,053,917 A * | 4/2000 | Sherman et al. | 606/270 |
| 6,063,090 A * | 5/2000 | Schlapfer | 606/270 |
| 6,074,391 A * | 6/2000 | Metz-Stavenhagen et al. | 606/278 |
| RE37,665 E * | 4/2002 | Ralph et al. | 606/278 |
| 6,440,137 B1 * | 8/2002 | Horvath et al. | 606/302 |
| 6,471,705 B1 * | 10/2002 | Biedermann et al. | 606/271 |
| 6,835,196 B2 | 12/2004 | Biedermann et al. | |
| 2001/0001119 A1 * | 5/2001 | Lombardo | 606/73 |
| 2003/0100896 A1 | 5/2003 | Biedermann et al. | |
| 2003/0125741 A1 | 7/2003 | Biedermann et al. | |
| 2003/0187439 A1 * | 10/2003 | Biedermann et al. | 606/61 |
| 2003/0199873 A1 * | 10/2003 | Richelsoph | 606/61 |
| 2004/0097933 A1 * | 5/2004 | Lourdel et al. | 606/61 |
| 2004/0172022 A1 * | 9/2004 | Landry et al. | 606/61 |
| 2004/0186474 A1 * | 9/2004 | Matthis et al. | 606/61 |
| 2004/0225289 A1 * | 11/2004 | Biedermann et al. | 606/61 |
| 2004/0249380 A1 * | 12/2004 | Glascott | 606/73 |
| 2004/0267264 A1 * | 12/2004 | Konieczynski et al. | 606/73 |
| 2005/0038433 A1 | 2/2005 | Young | |
| 2005/0055026 A1 | 3/2005 | Biedermann et al. | |
| 2005/0059972 A1 | 3/2005 | Biscup | |
| 2005/0215991 A1 | 9/2005 | Altman et al. | |
| 2005/0215998 A1 | 9/2005 | Donath | |
| 2005/0283244 A1 * | 12/2005 | Gordon et al. | 623/17.15 |
| 2006/0149232 A1 * | 7/2006 | Sasing | 606/61 |
| 2006/0155277 A1 | 7/2006 | Metz-Stavenhagen | |
| 2006/0200131 A1 * | 9/2006 | Chao et al. | 606/61 |
| 2007/0055240 A1 * | 3/2007 | Matthis et al. | 606/61 |
| 2008/0195159 A1 * | 8/2008 | Kloss et al. | 606/305 |

FOREIGN PATENT DOCUMENTS

| | | |
|---|---|---|
| CN | 1558742 A | 12/2004 |
| DE | 43 30 837 A1 | 3/1995 |
| DE | 4330837 A1 | 3/1995 |
| DE | 101 57 969 C1 | 2/2003 |
| DE | 10157969 C1 | 2/2003 |
| KR | 10-2003-0057315 | 7/2003 |
| KR | 10-2004-0054786 | 6/2004 |
| KR | 10-2005-0058992 | 6/2005 |
| WO | WO 98/27884 A1 | 7/1998 |
| WO | WO 03/043511 A1 | 5/2003 |
| WO | WO 03/096915 | 11/2003 |
| WO | WO 2005/122965 A2 | 12/2005 |

OTHER PUBLICATIONS

Partial translation of DE 43 30 837 A1.

* cited by examiner

BONE ANCHORING DEVICE

CROSS-REFERENCE TO RELATED APPLICATION(S)

The present disclosure claims priority from U.S. Provisional Patent Application Ser. No. 60/704,992, filed Aug. 3, 2005, and claims priority from European Patent Application EP05016901, filed Aug. 3, 2005, the entire disclosures of which are incorporated herein by reference.

BACKGROUND

The present disclosure relates to a bone anchoring device.

A bone anchoring device comprising a shank to be anchored in a bone and a receiving portion to connect the shank with a rod, wherein the receiving portion and the shank are formed as a single piece is known, for example, from U.S. Pat. No. 5,005,562 or from DE 101 57 969 C1. At the time of screwing in such a so-called monoaxial bone screw the receiving portion is aligned to receive the rod by rotating the shank within its fixation in the bone. The depth into which the shank can be screwed into the bone, depends on the required orientation of the receiving portion relative to the rod. Therefore, the possibility of fine-adjusting the orientation of the receiving portion relative to the rod depends on the thread pitch of the threaded shank. Usually monoaxial bone screws can not be screwed-in to be fully seated within the anatomical dimensions.

A polyaxial bone anchoring device, wherein the shank and the head are separate parts, is known from U.S. Pat. No. 6,835,196 E2. This bone anchoring device comprises a shank to be anchored in the bone and a head which has an exterior surface with a spherical segment-shaped portion, a receiving portion to receive said head and an element which exerts pressure on said head. The shank is received in a bore in the head which has a spring-yielding edge to clamp said end portion of the shank when pressure is exerted on the head. Since the head has an exterior surface with a spherical segment-shaped portion, the head can be pivoted in the receiving portion as long as a pressure is not exerted onto the head. With this bone anchoring device it is possible to first screw in the shank, adjust the length of the shank, if necessary, and then connect it with the receiving portion containing the head.

For certain clinical applications monoaxial bone screws are more appropriate than polyaxial bone screws. However, the known monoaxial bone screws have the disadvantage that there is only a small possibility of alignment of the receiving portion relative to the rod and yet be fully seated in the bone so as to be flush with the bone surface.

In view of the above, there is a need for a bone anchoring device that can remedy one or more of the above described problems associated with current bone anchoring devices.

SUMMARY

A bone anchoring device in accordance with the present disclosure includes an anchoring element which has a shank to be anchored in a bone and a head, a receiving portion to receive said head and an element which exerts pressure on said head, wherein said head and said receiving portion are connected such that a longitudinal axis of the receiving portion and the shank axis have a fixed angle relative to each other and wherein the receiving portion and the head are rotatable relative to each other.

In accordance with the present disclosure, a bone anchoring device of the monoaxial type provides an improved possibility of alignment of the receiving portion relative to the rod and yet be fully seated in the bone so as to be flush with the bone surface. Further, the bone anchoring device includes a simple construction and shall be easy to handle.

The bone anchoring device according to the present disclosure has a receiving portion that is easily adjustable relative to the rod in a range of 360° around the shaft axis independently from the depth to which the shank is screwed into the bone. The alignment is independent from the thread pitch of a bone thread provided at the shank. Therefore, the shank can be screwed into the bone to be fully seated therein so as to be flush with the bone surface.

The bone anchoring device according to the present disclosure provides a bone screw thread with a greater thread pitch compared to the conventional monoaxial bone screws or can provide a bone screw with multiple-threads.

With a bone anchoring device according to the present disclosure, it is possible to use the receiving portion and the shank of known polyaxial bone anchoring devices, such as disclosed in U.S. Pat. No. 6,835,196 B2 by simply combining it with the head according to the present disclosure to provide for a monoaxial bone screw.

Further features and advantages of the present disclosure will become apparent from the description of embodiments in conjunction with the accompanying drawings.

DETAILED DESCRIPTION

Figure 1:
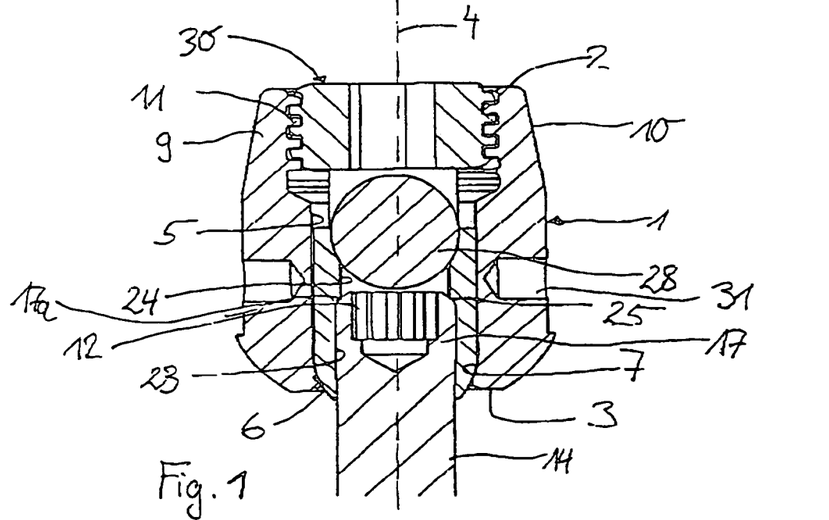
FIG. 1 shows a cross-sectional view of the bone anchoring device according to a first embodiment of the present disclosure.
Figures 2, 3:
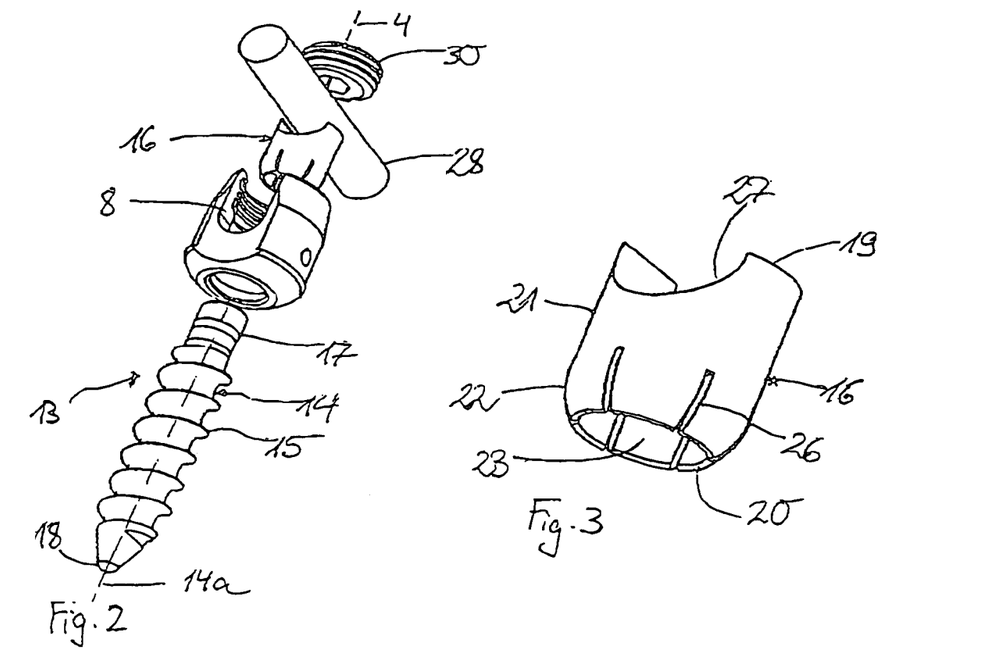
FIG. 2 shows an exploded view of the bone anchoring device according to FIG. 1.
FIG. 3 shows a perspective view of the head of the bone anchoring element, which is part of the bone anchoring device according to FIG. 1.

As shown in FIGS. 1 to 3, the bone anchoring device includes a receiving portion 1, which is substantially cylindrical and has a first end 2 and a second end 3 opposite to the first end. The two ends are perpendicular to a longitudinal axis 4. Coaxially with the longitudinal axis 4 a bore 5 is provided which extends from the first end 2 to a predetermined distance from the second end 3. At the second end 3 an opening 6 is provided, the diameter of which is smaller than the diameter of the bore 5. The coaxial bore 5 tapers towards the opening 6 in form of a spherically-shaped section 7.

The receiving portion 1 further has a U-shaped recess 8 which starts at the first end 2 and extends in the direction of the second end 3 to a predetermined distance from the second end 3. By means of the U-shaped recess, two free legs 9, 10 are formed ending towards the first end 2. Adjacent to the first end 2 the receiving portion 1 includes an internal thread 11 at the legs 9, 10.

The bone anchoring element 13 includes a shank 14 with a bone thread 15 and a head 16, which is formed as a separate part and which is connected to the shank in the assembled state shown in FIG. 1. The shank 14 has a shank axis 14a and includes a cylindrical end portion 17 to be received in the head 16 and a tip 18 on the opposite end. The cylindrical end portion is provided with a chamfer 17a to facilitate insertion into the head 16. At its end surface, the end portion includes a recess 12 for engagement with a screwing-in tool.

The head 16 is substantially cylindrically shaped and includes a first end 19 and a second end 20 opposite to the first end. As can be seen in particular in FIG. 3 the head 16 has a first portion 21 adjacent to the first end 19, having a cylindrical outer surface. The diameter of the first portion 21 is just as large that the head 16 can slide in the bore 5. Adjacent to the first portion 21, there is a second portion 22, in which the outer surface of the head 16 tapers towards the second end 20. In this embodiment, the second portion 22 has a spherical segment-shaped outer surface. The radius of the spherical segment corresponds to the radius of the spherical section 7 of the receiving portion 1 such that the head 16 rests with its second portion 22 or a part thereof in the spherical portion of the receiving portion 1. As can be seen in particular in FIG. 1, the head 16 further includes a first coaxial bore 23 extending from the second end 20 in direction to the first end 19. The diameter of the first coaxial bore 23 is just as large that the end portion 17 of the shank can be inserted into the bore from the second end 20. A second coaxial bore 24 is provided which extends from the end of the first bore 23 to the first end 19. The diameter of the second coaxial bore 24 is smaller than the diameter of the first coaxial bore 23 such that at the transition of the first bore 23 to the second bore 24 a circular abutment surface 25 is provided which forms a stop for the end portion 17 of the shank when the end portion 17 is inserted into the first coaxial bore 23 of the head 16.

In the second portion 22 of the head a plurality of slits 26 are provided which are open towards the second end 20 and extend through the second portion 22 to a predetermined distance from the second end 20. In the embodiment shown in FIG. 3 six slits 26 are provided which are spaced equidistantly in a circumferential direction. However, fewer or more slits can be provided. At least one slit is required to render the second portion elastic to clamp the end portion 17 of the shank. The second bore 24 allows for accessing the recess 12 provided at the end surface of the end portion 17 of the shank for screwing-in the shank into the bone with a screwing-in tool.

The head 16 further includes a cylindrical segment-shaped recess 27 starting at the first end 19 and extending in the direction to the second end 20. The cylinder axis of the recess 27 is perpendicular to the longitudinal axis 4. The radius of the recess 27 corresponds to the radius of a rod 28 to be received in the recess 27. The size of the recess 27 is such that when the rod 28 is inserted, it protrudes over the first end 19.

The bone anchoring device further includes an inner screw 30, which can be screwed-in between the legs 9, 10 to fix the rod 28 and to exert a pressure via the rod 28 on the head 16. The internal thread 11 and the cooperating thread of the inner screw 30 can have any known thread shape. A flat thread or a negative angle thread however, has the advantage that a splaying of the legs 9, 10 does not occur which makes it unnecessary to use an outer nut or a ring.

The length of the head 16 is such that in an assembled state shown in FIG. 1 the head 16 encompasses the end portion 17 of the shank with the spherical segment-shaped second portion 22 and a part of the cylindrical portion 21.

The parts of the bone anchoring device described above are preferably made of a body compatible material, such as for example, titanium.

In a first mode of operation, a shank 14 of suitable length and with a desired bone thread 15 is selected and connected with its end portion 17 to the head 16 by introducing it from the second end 20 of the head 16 into the first bore 23 until the end surface abuts to the abutment surface 25. The introduction of the end portion 17 into the head 16 from the second side 20 is facilitated by the chamfer 17a. The end portion 17 is provisionally held in the head 16 by means of friction.

Then, the bone anchoring element 13 consisting of the shank 14 with the mounted head 16 is introduced into the receiving portion 1 from the first end 2 with the threaded shank 14 being guided through the opening 6 of the receiving portion until the head 16 rests against the edge of the opening 6. The head and the shank are rotated such that the recess 27 of the head is aligned with the U-shaped recess 8 of the receiving portion. In such a preassembled state which can be loosely held by crimp bores 31 shown in FIG. 1, the shank is screwed into the bone with a screwing-in tool which engages the recess 12 in the end portion 17 through the second bore 24 in the head. The shank 14 can be fully screwed into the pre-drilled core hole without the necessity of alignment of the receiving portion during the screwing-in procedure.

When the shank is fully screwed-in, the receiving portion together with the head can be rotated around the longitudinal axis 4 by 360° to align it with respect to the rod 28 to be inserted. After aligning the receiving portion 1 the rod 28 is inserted until it rests in the cylindrical recess 27 of the head. Then the inner screw 30 is inserted and tightened until it presses onto the rod 28 which itself presses the head 16 against the spherical portion 7 of the receiving portion. By pressing the head 16 against the spherical section 7 of the receiving portion the spherical portion 22 of the head is compressed due to the slits 26 and firmly clamps the shank. At the same time, the head is pressed against the spherical portion 7 and locked relative to the receiving portion 1 in its rotational position.

In a second mode of operation, the threaded shank 14 is first screwed into the bone or into a vertebra. Then, the receiving portion 1 together with the loosely preassembled head 16 is pressed onto the end portion 17 of the shark projecting out of the bone. Thereafter, the receiving portion 1 is aligned such as to be able to receive the rod 28. Then the inner screw 30 is screwed-in to fix to the head and the rod.

With the bone anchoring device it is possible to use a shank 14 with a bone thread 15 having a larger thread pitch than conventional monoaxial bone screws. Also the use of multiple-threads for the bone thread is possible. Since the receiving portion can be rotated by 360° around the shaft axis, the shaft can be screwed-in to the maximum depth in the core hole.

It is further possible to use the receiving portion of conventional polyaxial bone screws together with the head and shank of this embodiment.

Figure 4:
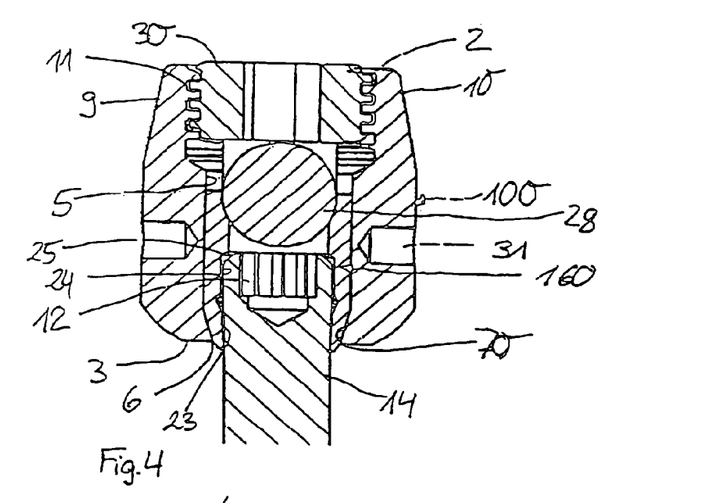
FIG. 4 shows a cross-sectional view of the bone anchoring device according to a second embodiment of the present disclosure.
Figure 5:
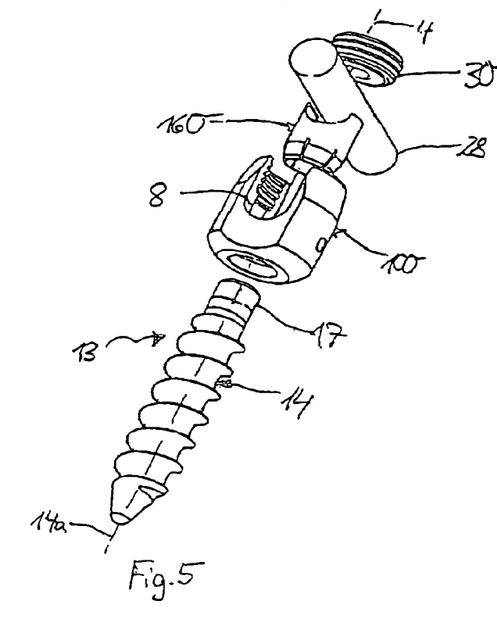
FIG. 5 shows an exploded view of the bone anchoring device according to FIG. 4.
Figure 6:
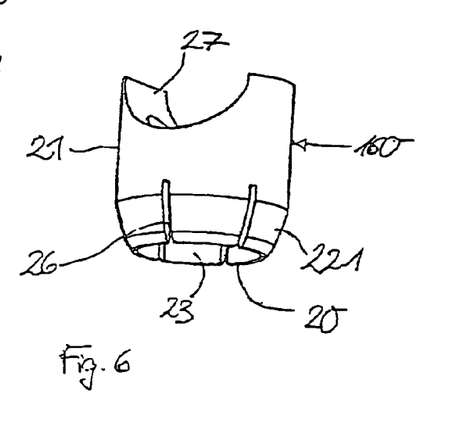
FIG. 6 shows a perspective view of the head of the bone anchoring element which is part of the bone anchoring device according to FIG. 4.

In the second embodiment shown in FIGS. 4 to 6, parts which are identical to the first embodiment are provided with the same reference signs as in the first embodiment. The second embodiment differs from the first embodiment in the shape of the section of the receiving portion against which the head rests and the shape of the head. The receiving portion 100 of the second embodiment has instead of the spherical segment shaped section 7 a conically tapering section 70 adjacent to the second end 3. Correspondingly the head 160 has a second portion 221 with an outer surface which conically tapers towards the second end 20. The cone angle of the second portion 221 of the head corresponds to the cone angle of the portion 70 of the receiving portion. The cone angle is selected such that in a preassembled state the receiving portion 100 is still rotatable relative to the head 160.

The modes of operation are identical to the first embodiment. Description thereof shall not be repeated.

The conical outer surface of the bone anchoring device of the second embodiment may be easier to manufacture than the spherical outer surface of the bone anchoring device of the first embodiment.

Modifications of the embodiments are possible. The diameter of the threaded portion of the shank 14 can be smaller or larger than the diameter of the end portion 17. The end portion 17 can have a conical shape such that the diameter increases towards the free end. The corresponding first bore 23 of the head can have a corresponding conical shape. In this case, the diameter of the first bore 23 is slightly smaller than the diameter of the end portion. The slits 26 allow an easy opening of the bore 23 and after inserting the end portion of the shank, the end portion is slightly clamped. The cone angle can be selected such that a self locking occurs when the shank is inserted into the head. The head can have one or more slits which are open towards the first end 19.

In a further modification, the head can be formed of a material providing elasticity, for example, a suitable plastic material. In this case, the slits may be omitted.

The receiving portion can also be modified. The radius of the spherical section 7 of the receiving portion of the first embodiment can be larger than the radius of the head, as long as the opening is small enough that the head cannot fall out. It is even possible to have a shape which is not spherical, but rounded or otherwise tapered towards the opening.

Figure 8:
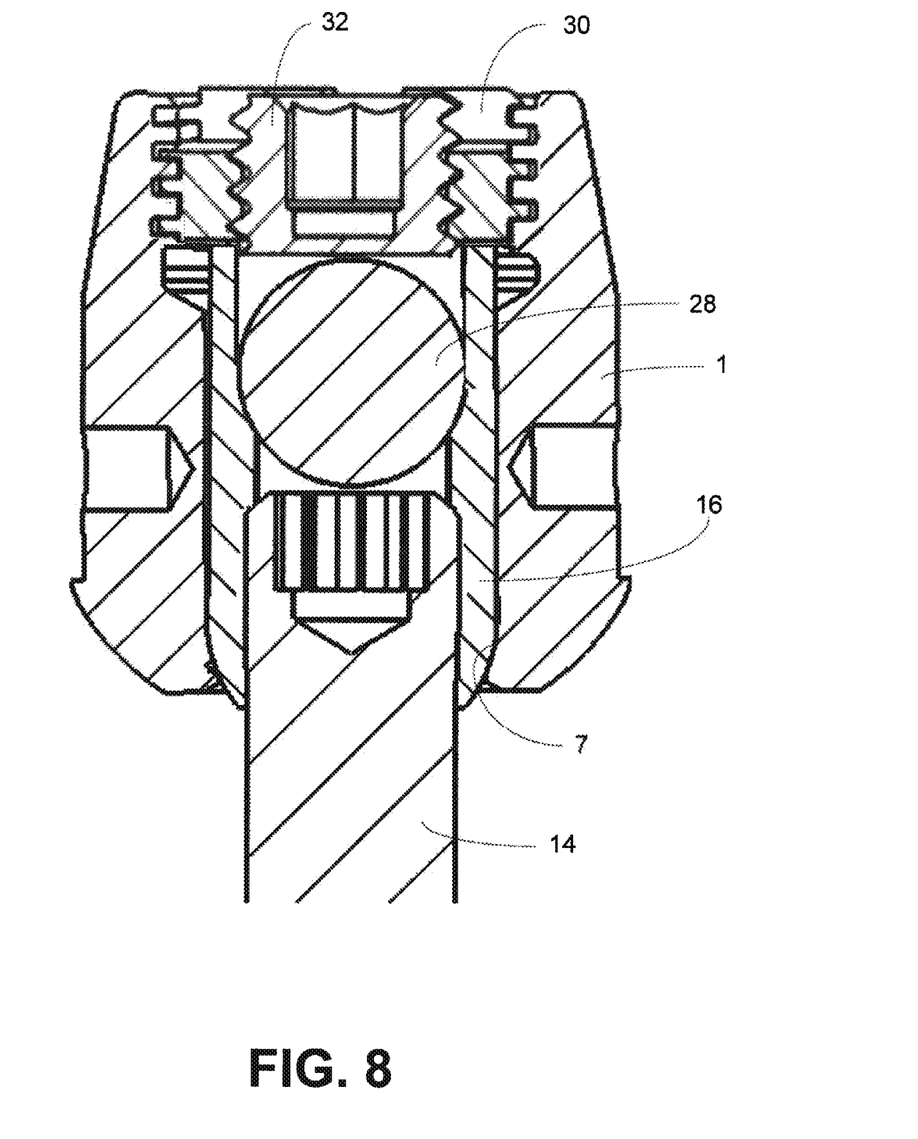
FIG. 8 shows a cross-sectional view of the bone anchoring device according to a fourth embodiment.

Referring to FIG. 8, the head 16 can have a U-shaped recess instead of the cylindrical recess 27 in such a way that by the U-shaped recess two free legs are formed. The dimensions of the U-shaped recess are such that the legs project above the rod 28 when the rod 28 is inserted. In this case it is possible to separately fix the head 16 via the inner screw 30 without fixing the rod 28. To fix the rod 28, a separate inner screw 32 is necessary.

The head also can have a flat free end surface.

Figure 7:
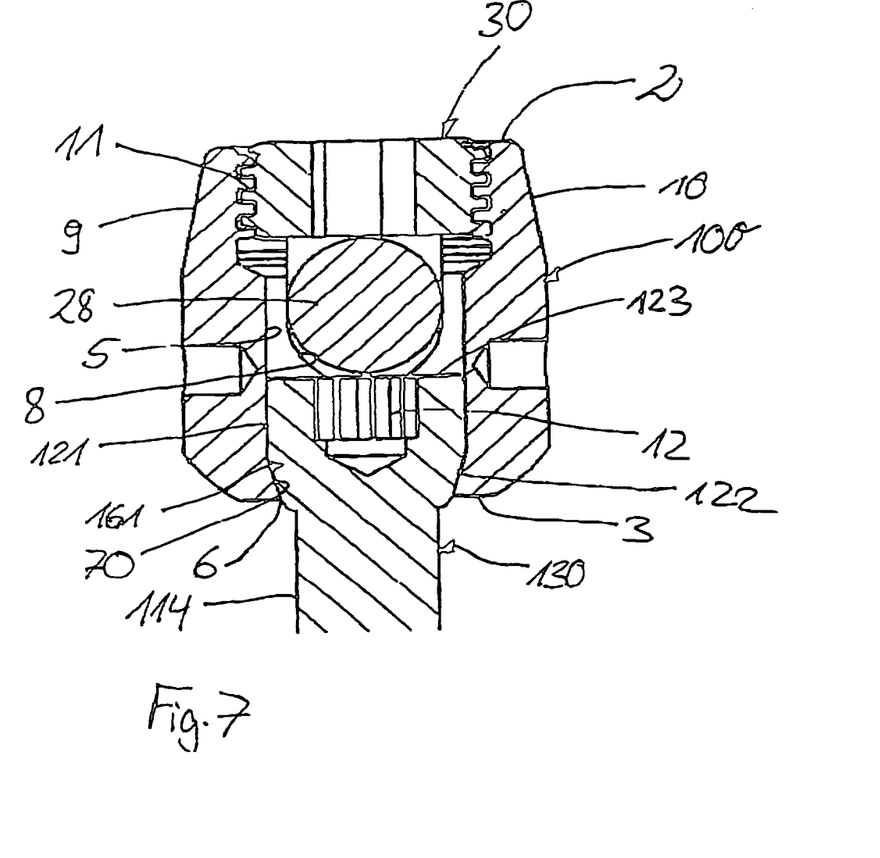
FIG. 7 shows a cross-sectional view of the bone anchoring device according to a third embodiment.

In the embodiments described the shank and the head are separate parts. However, the shank and the head can be formed as a single piece bone anchoring element. FIG. 7 shows a third embodiment which includes a bone anchoring element with a shank and a head formed as a single piece.

Parts of this embodiment which are identical to the second or first embodiment have the same reference numerals as those of the second or first element. The receiving portion 100 is shaped as the receiving portion of the second embodiment shown in FIG. 4 which has the conically tapering region 70 adjacent to the second end 3. The bone anchoring element 130 includes a shank 114 having a bone thread (not shown) and a head 161 formed as a single piece. The head 161 has a first portion 121 having a cylindrical outer surface and an adjacent second portion 122 having a conical outer surface tapering towards the shank. The diameter of the first portion is such that the head can slide in the bore 5 of the receiving portion 100. The cone angle of the conical portion 122 corresponds to that of the conical portion 70 of the receiving portion. The free end surface 123 of the head is flat and has a recess 12 for engagement with a screwing-in tool. The flat surface ensures that it is possible to align the receiving portion.

In use the bone anchoring element 130 is first inserted into the receiving portion 100, then it is screwed into the bone. When it is fully seated in the bone, the receiving portion is still rotatable with respect to the head and thus can be aligned to receive the rod. After inserting the rod 28 the inner screw 30 in tightened and exerts pressure on the rod 28 which exerts pressure on the head 161. The head is pressed against the opening 6 of the receiving portion or against the conical section 70 and is locked in its rotational position.

Modifications are possible. The conical section of the receiving portion can have another shape. The head can have, for example, a spherical section instead of the conical section.

While a particular form of the disclosure has been illustrated and described, it will be apparent that various modifications can be made without departing from the spirit and scope of the disclosure. Accordingly, it is not intended that the disclosure be limited, except as by the appended claims.

What is claimed is:

1. A bone anchoring device comprising:
   an anchoring element comprising a shank to be anchored in a bone or a vertebra and having a shank axis, and a head;
   a receiving portion comprising a first end and a second end opposite to the first end, a longitudinal axis passing through the two ends, and a first region adjacent to the second end for receiving a section of said head; and
   an element moveable between an unlocked position wherein the receiving portion and the shank are rotatable relative to each other and a locked position wherein the element exerts pressure on said head to lock said shank to the receiving portion to prevent rotation of the shank relative to the receiving portion, wherein when in the locked position, an end of the shank is positioned in the receiving portion, and at least a portion of the element is positioned along the longitudinal axis between an end face of the first end of the receiving portion that is farthest away from the second end of the receiving portion and an end face at the end of the shank in the receiving portion;
   wherein the receiving portion and the anchoring element are configured to form a monoaxial connection, the monoaxial connection comprising a fixed angle between the longitudinal axis of the receiving portion and the shank axis in both the unlocked and locked positions; and
   wherein the shank comprises an outer cylindrical or conical surface configured to contact and mate a matching inner surface of the head, and the receiving portion comprises an inner cylindrical or conical surface configured to contact and mate a matching outer surface of the head.

2. The bone anchoring device of claim 1, wherein said shank and said head are separate parts.

3. The bone anchoring device of claim 1, wherein said outer surface of said head comprises a cylindrical portion.

4. The bone anchoring device of claim 3, wherein said head has a portion which elastically clamps said shaft when pressure is exerted on the head.

5. The bone anchoring device of claim 1, wherein the head has a first end and a second end and a cylindrical recess extending from the first end in the direction of the second end to receive a rod.

6. The bone anchoring device of claim 1, wherein the head has a hollow interior portion to receive the shank.

7. The bone anchoring device of claim 6, wherein the head has a first end and a second end and a portion to clamp the shank tapers towards the second end.

8. The bone anchoring device of claim 7, wherein the portion to clamp the shank is spherically-shaped.

9. The bone anchoring device of claim 7, wherein the portion to clamp the shank is conically-shaped.

10. The bone anchoring device of claim 7, wherein the portion to clamp the shank comprises at least one slit.

11. The bone anchoring device of claim 1, wherein said first region of the receiving portion for receiving the head tapers towards the second end.

12. The bone anchoring device of claim 1, wherein the longitudinal axis of the receiving portion and the shank axis are coaxial.

13. The bone anchoring device of claim 1, wherein said head has a flat end surface.

14. The bone anchoring device of claim 1, wherein the element directly exerts pressure on said head.

15. The bone anchoring device of claim 1, wherein the element indirectly exerts pressure on said head.

16. The bone anchoring device of claim 1, wherein the head is non-spherical.

17. The bone anchoring device of claim 1, wherein the element is spaced apart from the shank along the longitudinal axis in both the unlocked and locked positions.

18. The bone anchoring device of claim 1, further comprising a rod, wherein the element is configured to simultaneously lock said rod and said shank to the receiving portion.

19. The bone anchoring device of claim 1, wherein the head is configured to be positioned at the end of the shank in the receiving portion in at least a locked position of the bone anchoring device.

20. The bone anchoring device of claim 1, wherein receiving portion includes a U-shaped recess at the first end extending in the direction of the second end.

21. A method of using a bone anchoring device, the bone anchoring device comprising an anchoring element comprising a shank to be anchored in a bone or a vertebra and having a shank axis, and a head, a receiving portion comprising a first end and a second end opposite to the first end, a longitudinal axis passing through the two ends, and a first region adjacent to the second end for receiving a section of said head, an element moveable between an unlocked position wherein the receiving portion and the shank are rotatable relative to each other and a locked position wherein the element exerts pressure on said head to lock said shank to the receiving portion to prevent rotation of the shank relative to the receiving portion, wherein when in the locked position, an end of the shank is positioned in the receiving portion, and at least a portion of the element is positioned along the longitudinal axis between an end face of the first end of the receiving portion that is farthest away from the second end of the receiving portion and an end face at the end of the shank in the receiving portion, wherein the receiving portion and the anchoring element are configured to form a monoaxial connection, the monoaxial connection comprising a fixed angle between the longitudinal axis of the receiving portion and the shank axis in both the unlocked and locked positions, and wherein the shank comprises an outer cylindrical or conical surface configured to contact and mate a matching inner surface of the head, and the receiving portion comprises an inner cylindrical or conical surface configured to contact and mate a matching outer surface of the head, the method comprising:

attaching the bone anchoring element and the receiving portion to a bone or a vertebra, the attaching comprising attaching the shank of the bone anchoring element to the bone or the vertebra, connecting the head of the bone anchoring element to the shank and connecting the head to the receiving portion forming the monoaxial connection;

rotating the receiving portion about a longitudinal axis of the receiving portion relative to the shank after forming the monoaxial connection;

inserting a rod in a recess of the head after aligning the recess of the head with a recess of the receiving portion upon rotating the receiving portion about the longitudinal axis of the receiving portion; and fixing the rod in the receiving portion with the element, wherein fixing the rod in the receiving portion fixes the shank and the receiving portion to prevent rotation of the shank relative to the receiving portion.

22. The method of claim 21, wherein attaching the bone anchoring element and the receiving portion to a bone or a vertebra comprises:

inserting the shank into a bore of the head from a second end of the head, wherein an end portion of the shank is frictionally held in the bore of the head proximate to a first end of the head;

connecting the head and the shank to the receiving portion, the connecting comprising inserting the head and the shank into an opening of the receiving portion, wherein the head rests against an edge of the opening; and attaching the shank to a bone or a vertebra.

23. The method of claim 21, wherein attaching the bone anchoring element and the receiving portion to a bone or a vertebra comprises:

attaching the shank to a bone or verterbra, wherein an end portion of the shank is exposed;

inserting the head into an opening of the receiving portion, wherein the head rests against an edge of the opening; and connecting the receiving portion and the head to the end portion of the shank, the connecting comprising pressing the end portion of the shank inside a bore of the head, and wherein the end portion of the shank is frictionally held in the head.

24. A bone anchoring device comprising:

an anchoring element comprising a shank to be anchored in a bone or a vertebra and having a shank axis, and a head;

a receiving portion comprising a first end and a second end opposite to the first end, a longitudinal axis passing through the two ends, a bore coaxial with the longitudinal axis, and a first region adjacent to the second end for receiving a section of said head; and an element moveable between an unlocked position wherein the receiving portion and the shank are rotatable relative to each other and a locked position wherein the element exerts pressure on said head to lock said shank to the receiving portion to prevent rotation of the shank relative to the receiving portion;

wherein the receiving portion and the anchoring element are configured to form a monoaxial connection, the monoaxial connection comprising a fixed angle between the longitudinal axis of the receiving portion and the shank axis in both the unlocked and locked positions; and wherein when the bone anchoring device is assembled and the element is in the unlocked position, the shank comprises an outer cylindrical or conical surface configured to contact and mate a matching inner surface of the head such that the shank is provisionally held in the head by friction, and the receiving portion comprises an inner cylindrical or conical surface configured to contact and mate a matching outer surface of the head.

25. The bone anchoring device of claim 24, wherein the head is further provisionally held in the receiving portion by friction when the bone anchoring device is assembled and the element is in the unlocked position.

26. A bone anchoring device comprising:

an anchoring element comprising a shank to be anchored in a bone or a vertebra and having a shank axis, and a head;

a receiving portion comprising a first end and a second end opposite to the first end, a longitudinal axis passing through the two ends, a bore coaxial with the longitudinal axis, and a first region adjacent to the second end for receiving a section of said head; and an element moveable between an unlocked position wherein the receiving portion and the shank are rotatable relative to each other and a locked position wherein the element exerts pressure on said head to lock said shank to the receiving portion to prevent rotation of the shank relative to the receiving portion;

wherein the receiving portion and the anchoring element are configured to form a monoaxial connection, the monoaxial connection comprising a fixed angle between the longitudinal axis of the receiving portion and the shank axis in both the unlocked and locked positions; and wherein when the bone anchoring device is assembled and the element is in the unlocked position, the shank comprises an outer cylindrical or conical surface configured to contact and mate a matching inner surface of the head, and the receiving portion comprises an inner cylindrical or conical surface configured to contact and mate a matching outer surface of the head, such that the head is provisionally held in the receiving portion by friction.

* * * * *

UNITED STATES PATENT AND TRADEMARK OFFICE
CERTIFICATE OF CORRECTION

| | | |
|---|---|---|
| PATENT NO. | : 8,696,712 B2 | Page 1 of 1 |
| APPLICATION NO. | : 11/498931 | |
| DATED | : April 15, 2014 | |
| INVENTOR(S) | : Biedermann et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 891 days.

Signed and Sealed this
Fourth Day of August, 2015

Michelle K. Lee
*Director of the United States Patent and Trademark Office*